United States Patent [19]

Van Pool

[11] 4,371,732

[45] Feb. 1, 1983

[54] ALKYLATION PROCESS

[75] Inventor: Joe Van Pool, Bartlesville, Okla.

[73] Assignee: Phillips Petroleum Company, Bartlesville, Okla.

[21] Appl. No.: 297,450

[22] Filed: Aug. 28, 1981

[51] Int. Cl.³ .............................................. C07C 2/58
[52] U.S. Cl. .................................................. 585/723
[58] Field of Search ........................................ 585/723

[56] References Cited

U.S. PATENT DOCUMENTS

| | | | |
|---|---|---|---|
| 2,910,521 | 10/1959 | Cobb, Jr. | 585/701 |
| 3,233,007 | 2/1966 | Chapman | 585/720 |
| 4,180,526 | 12/1979 | Chapman | 585/719 |
| 4,182,924 | 1/1980 | Chapman | 585/712 |
| 4,189,616 | 2/1980 | Liebert | 585/701 |

Primary Examiner—Curtis R. Davis

[57] ABSTRACT

An alkylation process comprising fractionating the hydrocarbon phase separated from the alkylation effluent into an overhead condensate comprising at least three portions wherein one portion is subjected to depropanization, another portion is used as reflux for the fractionating, and another portion is recycled to the alkylation.

6 Claims, 1 Drawing Figure

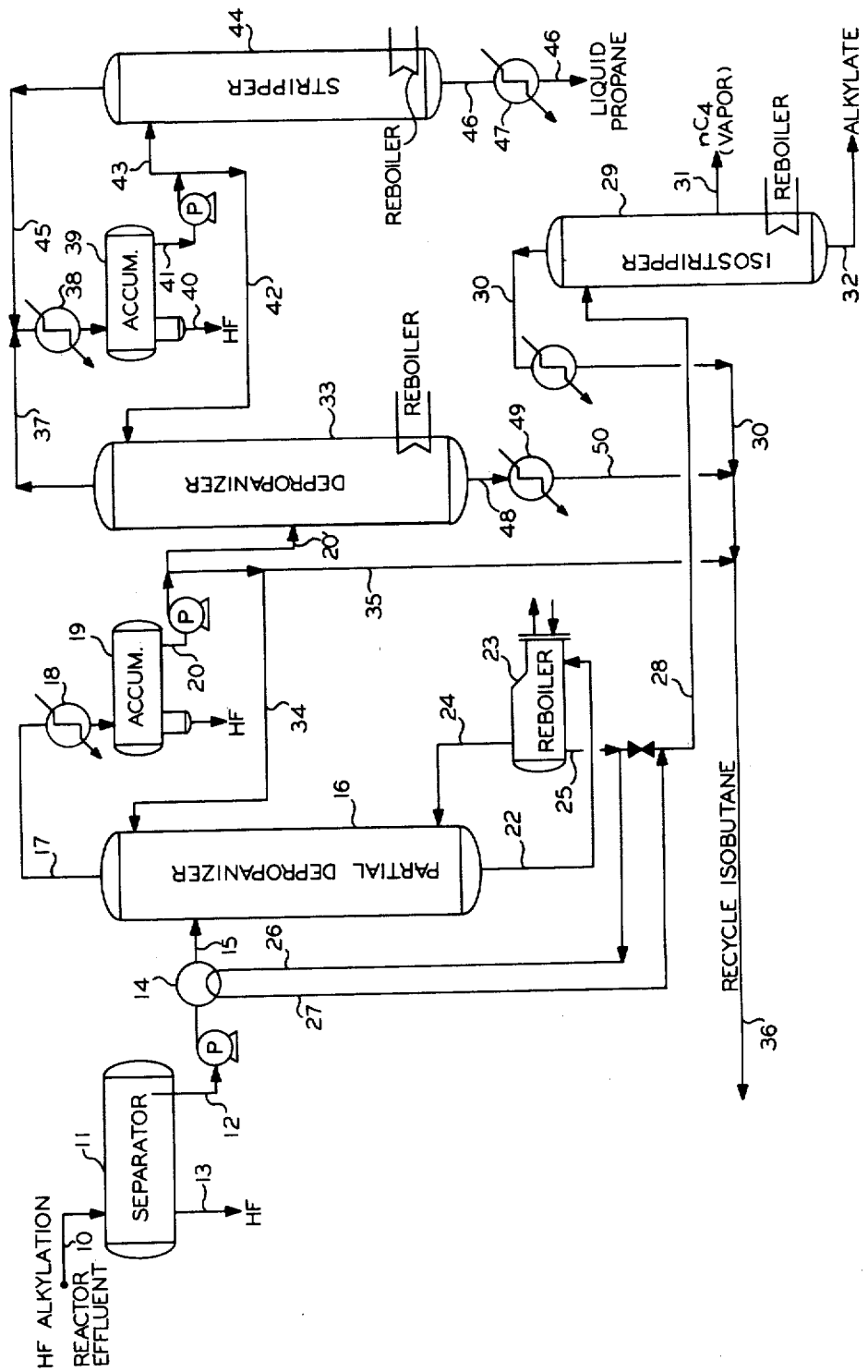

ALKYLATION PROCESS

This invention relates to an HF alkylation process and the recovery of the produced hydrocarbon phase in a more efficient manner. In one of its aspects, the invention relates to the alkylation of an isoparaffin with an olefin in the presence of HF acid. In a more specific aspect, this invention relates to the utilization of at least a portion of the condensed overhead, removed from the first fractionation of the alkylation hydrocarbon effluent as part of the isoparaffinic recycle to the alkylation unit.

As is well known, hydrocarbon products can be produced by alkylation reactions involving the combination or condensation of two dissimilar hydrocarbon reactants in the presence of suitable catalytic agents. Although various types of alkylate products can be obtained by employing various types of reactants, the alkylation of low boiling isoparaffins, such as isobutane, with low boiling olefins, such as propylene, butylenes, and the like, for the production of various fuels has become of particular importance. Liquid hydrogen fluoride (hydrofluoric acid) has found favor as a catalyst in this type of reaction.

The alkylation of isobutane with olefins is representative of this type of reaction and has been commonly carried out by feeding isobutane and olefin feedstocks in the liquid state along with hydrofluoric acid to an alkylation reactor such as a riser-reactor. Reaction product stream is then passed to various separation zones, such as an HF stripper, an isostripper, a depropanizer, and the like, in order to recover the various components of the hydrocarbon phase separated from the alkylation effluent. Energy requirements for heating the various separation zones and streams are great and it would be desirable, due to the high cost of energy, to use an energy-conserving alkylation process. The present invention is directed to such an energy-conserving process.

Accordingly, an object of this invention is to provide an improved alkylation process.

A further object of this invention is to reduce the energy costs in an HF alkylation fractionation system.

Other aspects, objects, and the several advantages of the invention will become apparent to those skilled in the art upon a study of the specification, the drawing, and the appended claims to the invention.

In accordance with the invention, an HF alkylation fractionation system is provided for the separation of a hydrocarbon liquid phase separated from an alkylation effluent comprising a partial or predepropanizer, a depropanizer, a propane stripper, and an isostripper, wherein at least a portion of the overhead from the partial depropanizer is used at least a portion of the recycled isoparaffin to the alkylation reaction along with isoparaffin recovered from the isostripper and the depropanizer.

This invention relates to an alkylation process involving the contacting of an olefin and isoparaffin in the presence of an acid alkylation catalyst under such alkylation conditions as to form an alkylate-containing alkylation effluent. In a specific embodiment, the alkylation process comprises contacting a butylenes stream containing varying amounts of propylene, as the olefin stream, and isobutane, as the isoparaffin.

In the embodiment just mentioned, the hydrocarbon effluent, removed from the alkylation unit phase separation zone, is charged to a partial depropanizer operated under conditions sufficient to take overhead HF, propane, and isobutane with a minimum quantity of normal butane and a bottoms stream comprising isobutane, substantial normal butane, and alkylate. The bottoms stream is passed to an isostripper operated under conditions to remove alkylate as bottoms product, normal butane as a side stream, and isobutane as overhead for recycle to the alkylation reaction. The overhead removed from the partial depropanizer is condensed and separated into a hydrocarbon phase comprising primarily isobutane, propane, and some HF wherein at least a portion is recycled to the partial depropanizer as reflux, another portion passed as recycle to the alkylation unit, and the remainder passed to a depropanizer wherein the remainder is separated into a net propane fraction, and HF for reuse as desired.

For sake of brevity, the invention will be described in terms of "isobutane". It will be understood by one skilled in the art in possession of this disclosure having studied the same that the invention, in its essential concepts, is applicable to other than "isobutane", for example, to other isoparaffins, paraffins, or related or other hydrocarbons or materials which are extant in an overall operation as herein described.

The preferred olefins in the process comprise butylenes, which can contain $C_3$ hydrocarbons such as propylene and propane. The amount of $C_3$ hydrocarbons present in the butylenes feed can vary appreciably but ordinarily will be in the range of about 5 to 25 volume percent, preferably about 2 to 10 volume percent.

The alkylation temperature can range from about 40° F. to about 120° F. However, when alkylating isobutane with a butylene stream, using a hydrogen fluoride catalyst, a reaction temperature in the approximate range of 60° F. to 100° F., with 90° F. now being preferred in order that cooling tower cooling water can be used to cool the recirculated HF catalyst charged to the HF alkylation. Cooler temperatures in butylenes alkylation produce higher octane alkylate.

The mole ratio of isoparaffin to olefin is generally maintained in the range of 4:1 to 20:1, preferably about 8:1 to 12:1. The volume ratio of acid to hydrocarbon feed, particularly when using HF acid, is maintained at about 0.2:1 to 10:1, preferably about 3:1 to 5:1.

A better understanding of the invention will be obtained by reference to the accompanying drawing, which shows an arrangement of an apparatus representing a preferred embodiment of the invention.

Referring to the drawing, an HF alkylation liquid hydrocarbon-HF effluent emulsion stream 10 is passed to phase separation zone 11 wherein the effluent is allowed to separate into an upper liquid hydrocarbon phase which is removed by line 12 and a lower liquid HF acid phase which is removed by way of line 13 for recycle to the alkylation as desired. The alkylation reaction effluent in line 10 is produced from an alkylation zone (not shown) when a liquid olefin feed, such as a butylenes mixture, containing $C_3$'s, such as propylene and propane, is contacted with liquid isobutane in the presence of liquid HF catalysts. The particular type of reactor is not important and various appropriate reactors are well known in the art. One type of reactor often used is a riser-reactor, as disclosed in U.S. Pat. No. 3,213,157.

The hydrocarbon phase, removed by line 12 from separator 11, is passed through indirect heating exchanger 14 and thence through line 15 and introduced into partial depropanizer 16.

Partial depropanizer 16 is operated under conditions such that the overhead stream 17 comprises propane, HF, isobutane, and with very little normal butane, which is subjected to condensation in indirect condenser 18 and then introduced into accumulator 19 wherein the overhead is separated into an upper liquid hydrocarbon phase, removed by line 20, and a lower liquid HF phase removed by line 21 for reuse in the HF alkylation, as desired.

Representative operating conditions in partial depropanizer 16 include:

|  | Range | Specific |
|---|---|---|
| Pressure, psig | 130 to 270 | 160 |
| Temperature, °F. |  |  |
| Top, | 120 to 180 | 130 |
| Bottom, | 165 to 220 | 170 |

Partial depropanizer 16 is operated such that most of the normal butane, a substantial portion of the isobutane, and the alkylate product, are removed as bottoms from the partial depropanizer 16 by way of line 22, and passed through reboiler 23; a portion of the bottoms vaporized in reboiler 23 is passed by line 24 and reintroduced into the partial depropanizer 16. The remainder of the bottoms stream passed through reboiler 23 is removed as liquid by line 25 and, preferably, at least a portion is passed through indirect heat exchanger 16 by way of lines 26 and 27. The thusly-cooled bottoms stream is then passed by line 28 to isostripper column 29 operated under conditions such that isobutane is removed overhead by line 30 for recycle to the alkylation unit, normal butane vapor is removed as a side stream by line 31, and alkylate is removed as bottoms by line 32.

Isostripper 29 is conventional and typical operating conditions include

| Pressure, psig | 125 |
|---|---|
| Temperature, °F. |  |
| Top, | 135 |
| Bottom, | 350 |

Returning to the overhead removed from partial depropanizer 16, the hydrocarbon stream 20 removed from accumulator 19 comprises HF, propane, and isobutane, and in part is passed via 20' to depropanizer 33. A portion of the liquid overhead hydrocarbon stream is returned as reflux to partial depropanizer 16 by way of line 34. Another portion of the overhead hydrocarbon stream is passed by way of line 35 for recycle to the alkylation unit through line 36.

Depropanizer 33 is conventional and is operated under conditions such that propane and HF are taken overhead by line 37, passed through indirect condenser 38, and introduced into accumulator 39 wherein the overhead is allowed to separate into a lower liquid HF phase removed by line 40 for recycle to the alkylation, and an upper liquid hydrocarbon phase by line 41. A portion of this hydrocarbon phase is returned as reflux by line 42 to depropanizer 33 and the remainder or yield passed by line 43 to a conventional propane stripper 44. Propane stripper 44 is operated under conditions such that HF and some propane are taken overhead as vapor by line 45 and returned through indirect condenser 38 to accumulator 39. Propane liquid is removed from the system as bottoms from stripper 44 by way of line 46.

The propane stream is cooled by passage through indirect heat exchanger 47, prior to further processing, e.g., KOH treatment to remove residual HF.

The bottoms stream, rich in isobutane, is removed from depropanizer 33 by way of line 48 is cooled in indirect heat exchanger 49 and then passed through line 50 and combined with isobutane in lines 30, 35, and 36 for recycle to the HF alkylation unit.

The isoparaffin to olefin ratio maintained in the alkylation zone ordinarily is in the range of about 2 to about 20. This range is the total ratio of all recycle streams plus fresh or feed isoparaffin and isoparaffin in the olefin feed to the alkylation.

SPECIFIC EXAMPLE

A calculated example is herewith given in order to illustrate one set of possible operating conditions in accordance with the invention.

| Calculated Example (Best Mode) | |
|---|---|
| (15) Feed to Partial Depropanizer (16): | |
| Barrels/Day | 15,600 |
| Composition, vol. % | |
| Propane, | 3.9 |
| Isobutane, | 69.4 |
| Normal Butane, | 12.3 |
| (a) Isopentane plus, | 14.4 |
| (20') Feed to Depropanizer (33): | |
| Barrels/Day | 2544 |
| Composition, vol. % | |
| Propane, | 10.65 |
| Isobutane, | 79.89 |
| Normal Butane, | 9.46 |
| (35) Recycle to Alkylation Unit: | |
| Barrels/Day | 1512 |
| Composition, vol. % | |
| Propane, | 10.65 |
| Isobutane, | 79.89 |
| Normal Butane, | 9.46 |
| (28) Feed to Isostripper (29): | |
| Barrels/Day | 42,264 |
| Composition, vol. % | |
| Propane, | 3.2 |
| Isobutane, | 68.5 |
| Normal Butane, | 12.4 |
| Alkylate, | 15.9 |
| (32) Alkylate Yield: | |
| Barrels/Day | 7512 |
| Composition, vol. % | |
| Isobutane, | 15.0 |
| Normal Butane, | 0.6 |
| Alkylate, | 84.4 |
| (30) Isobutane Recycle: | |
| Barrels/Day | 34,776 |
| Composition, vol. % | |
| Propane, | 3.9 |
| Isobutane, | 83.1 |
| Normal Butane, | 11.9 |
| Isopentane | 1.1 |
| (48) Isobutane Recycle: | |
| Barrels/Day | 2280 |
| Composition, vol. % | |
| Propane, | 2.1 |
| Isobutane, | 87.4 |
| Normal Butane, | 10.5 |
| (46) Propane Yield: | |
| Barrels/Day | 264 |
| Composition, vol. % | |
| Propane, | 99.0 |
| Isobutane, | 1.0 |

(a) (Referred to as alkylate)

I claim:

1. An alkylation process comprising the steps of contacting an olefin stream comprising butylenes containing $C_3$ hydrocarbons and an isoparaffin comprising isobutane with an HF acid alkylation catalyst under alkylation conditions to form an alkylate-containing alkylation effluent, passing said effluent to a phase separation zone and allowing said effluent to separate into a hydrocarbon phase and an HF acid catalyst phase, passing said hydrocarbon phase to a partial depropanizing zone wherein the hydrocarbon phase is separated into an overhead stream comprising propane, HF, and some isoparaffin, and a bottoms stream substantially free of HF comprising isoparaffin, normal paraffin, and alkylate, condensing said overhead stream and passing at least a portion of the hydrocarbon condensate formed to a depropanizing zone operated under conditions to recover separately propane, HF, and isoparaffin for recycle to the alkylation, passing another portion of said condensate as reflux to said partial depropanizer, and passing the remainder of said condensate as at least a portion of the isoparaffin recycle to said alkylation.

2. A process according to claim 1 wherein said bottoms stream, removed from said partial depropanizer, is passed to an isostripper operated under conditions to remove isoparaffin overhead for recycle to said alkylation, a normal paraffin side stream, and an alkylate product bottoms stream.

3. A process according to claim 1 wherein said condensate stream, recycled to said alkylation, is so regulated as to allow a yield portion to be charged to depropanizing to prevent buildup of propane in the HF alkylation as by being recycled in the isobutane.

4. A process according to claim 1 wherein said condensate passed to said depropanizer is subjected to separation conditions in said depropanizer sufficient to remove propane and HF overhead which is condensed, separated into an HF and a hydrocarbon phase, which hydrocarbon phase is passed to a propane stripper for removal of HF and recovery of propane as bottoms product.

5. A process according to claim 1 wherein said olefin feed to said alkylation comprises butylenes containing 5 to 25 percent $C_3$ hydrocarbons including propylene and propane.

6. A process according to claim 1 wherein the amount of isoparaffin recycled to said alkylation from said depropanizer zone and said condensate are recycled to the alkylation at a rate such as to maintain an isoparaffin to olefin ratio in the range of 2 to 20.

* * * * *